United States Patent
Franzke et al.

(10) Patent No.: US 8,729,291 B2
(45) Date of Patent: May 20, 2014

(54) METHOD FOR PRODUCING URETHANES COMPOSED OF DI-FUNCTIONAL AROMATIC AMINES AND DIALKYL CARBONATES

(75) Inventors: Axel Franzke, Mannheim (DE); Robert Baumann, Mannheim (DE); Michael Bock, Ruppertsberg (DE); Roderich Roettger, Langenhagen (DE); Andreas Leitner, Pittsburg, PA (US); Matthias Kloetzer, Kroppen (DE)

(73) Assignee: BASF SE, Ludwigshafen (DE)

( * ) Notice: Subject to any disclaimer, the term of this patent is extended or adjusted under 35 U.S.C. 154(b) by 344 days.

(21) Appl. No.: 13/058,026

(22) PCT Filed: Aug. 18, 2009

(86) PCT No.: PCT/EP2009/060644
§ 371 (c)(1),
(2), (4) Date: Feb. 8, 2011

(87) PCT Pub. No.: WO2010/020621
PCT Pub. Date: Feb. 25, 2010

(65) Prior Publication Data
US 2011/0137067 A1  Jun. 9, 2011

(30) Foreign Application Priority Data
Aug. 22, 2008 (EP) .................... 08105102

(51) Int. Cl.
C07C 261/00 (2006.01)
(52) U.S. Cl.
USPC .......................................... 560/26
(58) Field of Classification Search
USPC ............................. 560/24, 25, 26
See application file for complete search history.

(56) References Cited

U.S. PATENT DOCUMENTS

| 3,763,217 | A |  | 10/1973 | Brill |  |
|---|---|---|---|---|---|
| 4,268,683 | A |  | 5/1981 | Gurgiolo |  |
| 4,268,684 | A |  | 5/1981 | Gurgiolo |  |
| 4,550,188 | A |  | 10/1985 | Frulla et al. |  |
| 5,773,643 | A | * | 6/1998 | Yagii et al. | 560/345 |
| 5,789,614 | A |  | 8/1998 | Yagii et al. |  |
| 2009/0082588 | A1 |  | 3/2009 | Polo et al. |  |

FOREIGN PATENT DOCUMENTS

| DE | 32 02 690 |  | 8/1982 |
|---|---|---|---|
| EP | 0 048 371 |  | 3/1982 |
| EP | 0 391 473 |  | 10/1990 |
| EP | 2 036 884 |  | 3/2009 |
| WO | 98 55451 |  | 12/1998 |
| WO | 98 56758 |  | 12/1998 |
| WO | WO9947493 | * | 3/1999 |
| WO | 99 47493 |  | 9/1999 |
| WO | WO9947493 | * | 9/1999 |
| WO | 2007 015852 |  | 2/2007 |

OTHER PUBLICATIONS

Parrill (1999).*
Reich (2002).*
Newman et al. (Reactions of 5,5-Disubstituted 3-Nitrosooxazolidones. New Syntheses of Vinyl Azides, Vinyl Isothiocyanates, Vinyl Diethyl Phosphonates, and Divinyl Ethers, J. Org. Chem., vol. 38, No. 14, pp. 2438-2441, 1973.).*
U.S. Appl. No. 13/163,928, filed Jun. 20, 2011, Rosendahl, et al.
International Search Report issued Oct. 28, 2009 in PCT/EP09/060644 filed Aug. 18, 2009.
U.S. Appl. No. 13/125,895, filed Apr. 25, 2011, Geissler, et al.
U.S. Appl. No. 13/394,647, filed Mar. 7, 2012, Mattke, et al.
U.S. Appl. No. 13/501,621, filed Apr. 12, 2012, Franzke, et al.
U.S. Appl. No. 13/008,457, filed Jan. 18, 2011, Bock, et al.

* cited by examiner

Primary Examiner — Wu-Cheng Winston Shen
Assistant Examiner — Blaine G Doletski
(74) Attorney, Agent, or Firm — Oblon, Spivak, McClelland, Maier & Neustadt, L.L.P.

(57) ABSTRACT

A process for preparing urethanes by reacting aromatic diamines with a dialkyl carbonate, wherein the alkyl radical of the organic dialkyl carbonate comprises 2-18 carbon atoms and one or more heteroatoms and the reaction is performed in the presence of a catalyst.

21 Claims, 1 Drawing Sheet

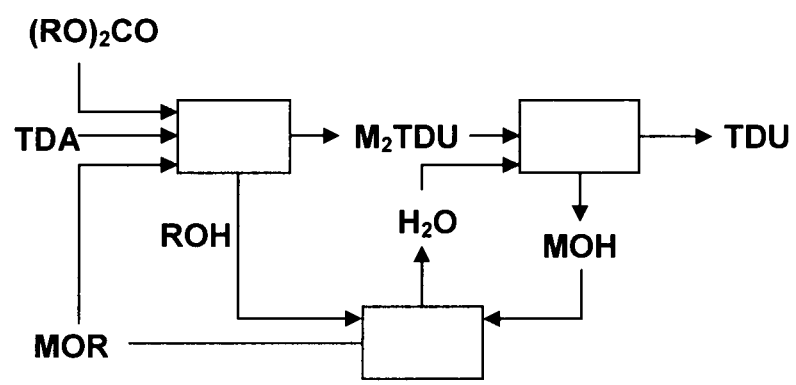

METHOD FOR PRODUCING URETHANES COMPOSED OF DI-FUNCTIONAL AROMATIC AMINES AND DIALKYL CARBONATES

CROSS REFERENCE TO RELATED APPLICATION

This application is a 371 of PCT/EP2009/060644, filed on Aug. 18, 2009, and claims priority to European Patent Application No. 08105102.1, filed on Aug. 22, 2008.

The invention provides a process for preparing bisurethanes by reacting difunctional aromatic amines with a dialkyl carbonate in high yields and selectivities. The urethanes thus prepared can subsequently be converted to industrially relevant isocyanates.

A range of processes for preparing urethanes is known.

In the reactions, for example, Lewis acids, for example uranium salts (U.S. Pat. No. 3,763,217), aluminum turnings with iodine and Hg promoters (U.S. Pat. No. 4,550,188), zinc salts, iron salts, antimony salts and tin salts (U.S. Pat. Nos. 4,268,683, 4,268,684, EP 391473) are used as catalysts. Disadvantages of the industrial use of these processes are the conversions, which are sometimes low, low selectivities or both.

High selectivities and yields are obtained, for example, in Lewis acid-catalyzed processes (Pb salts as catalysts) when a high excess of dialkyl carbonate (amine:carbonate 1:20) is used (WO 98/55451, WO 98/56758). The high excess of dialkyl carbonate leads to large recycle streams.

In other cases, high yields of urethane can be achieved when the urea formed in the urethanization is redissociated thermally in an additional reaction to the corresponding urethane (EP 048371 (catalysts: lead salts, titanium salts, zinc salts and zirconium salts), EP 391473 (catalyst: Zn salts)). The redissociation requires an additional, energy-intensive step.

A further disadvantage in the case of use of Lewis acids as homogeneous catalysts is the catalyst residues which remain in the product and can be removed only incompletely.

WO 2007/015852 describes the use of Lewis-acidic heterogeneous catalysts for the urethanization of aromatic amines. This dispenses with a complicated removal of a homogeneous catalyst. The conversions obtained are too low for industrial scale applications and, together with the selectivity, decrease with increasing service life of the heterogeneous catalyst.

It is additionally known that urethanes can be prepared from aromatic amines using basic compounds, for example alkali metal or alkaline earth metal alkoxides.

DE 3202690 describes the preparation of aromatic urethanes by reaction of aniline and dialkyl carbonates in the presence of a small amount of a metal alkoxide as a catalyst. The conversions described in the examples, in which aromatic monoamines were used, are incomplete and the selectivities achieved are insufficient for an industrial application.

Journal of Organic Chemistry, 2005, 70, 2219-2224 describes the reaction of aniline with a large excess of dimethyl carbonate (40-fold excess) in the presence of an excess of base such as sodium methoxide (NaOMe) or potassium tert-butoxide (KOtBu). A selectivity of 67% after a reaction time of 210 min was obtained with NaOMe. A selectivity of 100% after 1 min is described with KOtBu, but decreases with increasing reaction time to 60% as a result of formation of the N-methylcarbanilate by-product. Conversions and isolated yields were not described.

It is an object of the invention to develop a process for preparing urethanes from difunctional aromatic amines which enables a urethanization reaction in high space-time yields and selectivities. The urethanes prepared shall subsequently be processable to industrially important aromatic isocyanates.

The invention provides a process for preparing urethanes by reacting aromatic diamines with aromatic dialkyl carbonates, wherein the alkyl radical of the organic dialkyl carbonate comprises 2-18 carbon atoms and one or more heteroatoms and the reaction is performed in the presence of a catalyst.

The catalyst is preferably a base.

The heteroatoms are preferably halogens, especially chlorine or fluorine, oxygen and nitrogen. In the case of oxygen, it is preferably incorporated as an ether group. The nitrogen atoms are preferably incorporated as tertiary amino groups.

The heteroatoms are preferably present on the β-carbon atom.

The alkyl groups may comprise one or more heteroatoms. In the case of the halogen atoms, they may be present on one or more carbon atoms. The alkyl radicals may also comprise aromatic rings.

The reaction product formed from the aromatic amine with the dialkyl carbonate is preferably reacted with a protic compound.

A protic compound is understood to mean a compound which can transfer a proton.

The protic compound is preferably selected from the group comprising alcohols, water and mixtures of the two. Particular preference is given to the use of water.

The base is preferably used in a molar ratio of from 0.05 to 0.5 based on the amino groups, more preferably in a molar ratio of from 0.05 to 0.3 based on the amino groups.

The dialkyl carbonate is preferably used in a molar ratio of dialkyl carbonate to amino groups of from 1:1 to 10:1, more preferably from 1:1 to 3:1.

The reaction of the aromatic amine with the dialkyl carbonate in the presence of the base is preferably performed at a reaction temperature of 60-200° C., more preferably at 100-170° C. At this temperature, a quantitative conversion of the aromatic amine to the corresponding urethane can be obtained within 0.5-5 h. The reaction is typically performed under standard pressure, slightly elevated pressure or slightly reduced pressure.

In the process according to the invention, mono- and/or difunctional aromatic amines which preferably do not bear any heteroatoms in the aromatic radical are used. Representatives from this group are, for example, aniline, o-, m-, p-toluidine, o-, m-, p-chloroaniline and isomer mixtures, o-, m-, p-bromoaniline and isomer mixtures, o-, m-, p-trifluoromethylaniline and isomer mixtures, 2,4-, 2,6-, 3,4- and 3,5-dimethyl-, -dichloro-, -dibromo- and -diethylaniline and isomer mixtures, p-t-butylaniline, tolylenediamine (TDA), especially 2,4- and 2,6-tolylenediamine and isomer mixtures thereof, diaminophenylmethane (MDA), especially 2,4'-diaminophenylmethane, 4,4'-diaminophenylmethane, 2,2'-diaminophenylmethane and higher homologs (polyaminopolyphenylmethanes) and isomer mixtures thereof, and m-phenylenediamine.

Preference is given to using the isomers of tolylenediamine and/or the isomers of diaminophenylmethane.

The alkyl chain of the dialkyl carbonate may be unbranched, branched or cyclic. The alkyl chain is preferably branched or unbranched.

In one embodiment, the β-position of the alkyl chain is modified with an oxygen atom. This atom is preferably present in the form of an ether group.

In a preferred embodiment of the invention, the dialkyl carbonates are selected from the group comprising bis-2-methoxyethyl carbonate, bis-2-ethoxyethyl carbonate, bis-2-butoxyethyl carbonate, bis-2-methoxy-1-methylethyl carbonate, bis-2-methoxy-2-methylethyl carbonate Other examples: bis-2-trifluoroethyl carbonate and bis-2-N,N'-dimethylaminoethyl carbonate.

The base preferably comprises basic organic metal compounds, especially compounds of alkali metals. These may, for example, be compounds comprising nitrogen atoms, for example amides such as sodium amide, or compounds comprising silicon atoms and nitrogen atoms, for example lithium hexamethyldisilazide.

The base more preferably comprises the alkoxides of alkali metals.

The alcohol of the metal alkoxide has 2-18, more preferably 2-7, carbon atoms in the alkyl chain. The alkyl chain may be unbranched, branched or cyclic.

In one embodiment of the invention, the alkyl chain of the corresponding alcohol of the alkoxide is modified with heteroatoms. The heteroatoms may be halogen atoms, preferably fluorine atoms and/or chlorine atoms, more preferably fluorine atoms. In another embodiment, the heteroatoms are oxygen atoms. These are preferably present in the form of ether groups.

In a particularly preferred embodiment of the process according to the invention, the dialkyl carbonates and the metal alkoxides are based on the same alcohol. This has the advantage that a smaller amount of compounds is present in the process according to the invention. This reduces the complexity in the process.

In a preferred embodiment of the process according to the invention for preparing urethanes, in which water is used as the protic compound, the process according to the invention comprises the steps of
a) reacting the aromatic amine with the organic carbonate in the presence of a base
b) reacting the reaction products from step a with water
c) separating the products formed in step b) and the aqueous base
d) converting the aqueous base from step c) to the corresponding nonaqueous base and recycling it into step a)
e) isolating the urethane removed in step c).

This process can preferably be performed continuously.

In step b), the urethane is formed.

This embodiment is shown in FIG. 1 for use of water as the protic compound and an alkoxide as the base.

The urethane can be isolated as a solution in an organic solvent or as a pure substance in the form of a melt or of a solid.

The products formed in step b) are the urethane and, in the case of use of alkoxides as the base, the alkoxide.

Process step a) is performed in stage 1 of FIG. 1, process step b) in stage 2. In the case of batchwise mode, stages 1 and 2 can be carried out in the same reaction vessel, and in the case of continuous mode preferably in different reaction vessels.

The product from stage 1) can be transferred to stage 2) without further workup.

In stage 3), the aqueous base obtained in stage 2 is converted to the nonaqueous base; in the case of use of metal alkoxides, the hydroxide is converted to the metal alkoxide. The latter is recycled into stage 1. Excess alcohol obtained in stage 2 is discharged there or recycled at another point in the process.

The product from stage 2), if it is not already in this form, is separated into a nonaqueous phase and an aqueous phase. The urethane is removed from the organic phase which comprises it and is isolated as a solid or melt or used directly in this form in further reaction stages, for example in a thermal cleavage to the corresponding isocyanate. The urethanes removed can, if necessary, be purified, for example by washing.

In this invention, it has been shown that the inventive reaction of aromatic amines with a small excess of dialkyl carbonate is possible in high selectivities and high space-time yields. The urethanes are formed in high purities, and so no complicated further purification is required.

The invention will be illustrated in detail by the examples which follow.

EXAMPLE 1

6.1 g (50 mmol) of 2,4-diaminotoluene, 1.0 g (10 mmol) of sodium 2-methoxyethoxide, 2.4 g (32 mmol) of dry 2-methoxyethanol and 35.6 g (200 mmol) of bis(2-methoxyethyl) carbonate were weighed successively under argon into a 250 ml four-neck flask with stirrer, reflux condenser, internal thermometer and protective gas blanketing, which was immersed into an oil bath preheated to 120° C. After the mixture had been stirred at this temperature for 24 h, it was diluted with 100 ml of toluene and cooled to 50° C., and then 25 ml of water were metered in. On completion of phase separation, the organic upper phase was washed once with 25 ml of water and concentrated to dryness. A brown, high-viscosity oil was obtained (19.1 g), which, according to NMR spectroscopy, as well as carbonate residues, consisted for the most part of the desired bisurethane and only traces of the intermediate monourethanes (molar ratio of bisurethane to monourethanes of ≥95:≤5).

COMPARATIVE EXAMPLE 1

6.1 g (50 mmol) of 2,4-diaminotoluene, 0.82 g (10 mmol) of sodium n-propoxide, 2.0 g (33 mmol) of dry n-propanol and 29.2 g (200 mol) of di-n-propyl carbonate were weighed successively under argon into a 250 ml four-neck flask with stirrer, reflux condenser, internal thermometer and protective gas blanketing, which was immersed into an oil bath preheated to 120° C. After the mixture had been stirred at this temperature for 24 h, it was diluted with 100 ml of toluene and cooled to 50° C., and then 25 ml of water were metered in. On completion of phase separation, the organic upper phase was washed once with 25 ml of water and concentrated to dryness. A brown, high-viscosity oil was obtained (13.8 g), which, according to NMR spectroscopy, as well as carbonate residues, comprised both the bisurethane and monourethanes in a molar ratio of 65:35.

EXAMPLE 2

6.1 g (50 mmol) of 2,4-diaminotoluene, 1.5 g (15 mmol) of sodium 2-methoxyethoxide, 3.6 g (47 mmol) of dry 2-methoxyethanol and 35.6 g (200 mmol) of bis(2-methoxyethyl) carbonate were weighed successively under argon into a 300 ml autoclave with stirrer, which was placed into a thermostated heating jacket. After the mixture had been stirred at 140° C. for 2.5 h, 100 ml of toluene were added by means of a pump and the mixture was cooled to 50° C. The suspension was rinsed out of the autoclave with a further 50 ml of toluene, and 25 ml of water were added. On completion of phase separation, the organic upper phase was washed once with 25 ml of water. The collected water phases were reextracted with 100 ml of toluene, and the combined organic phases were concentrated to dryness. A brown, high-viscosity oil was obtained (16.3 g), which, according to NMR spectroscopy, as well as carbonate residues, consisted for the most part of the desired bisurethane and only traces of the intermediate monourethanes (molar ratio of bisurethane to monourethanes of ≥95:≤5).

COMPARATIVE EXAMPLE 2

12.2 g (100 mmol) of 2,4-diaminotoluene, 1.6 g (20 mmol) of sodium n-propoxide, 3.8 g (64 mmol) of dry n-propanol and 58.5 g (400 mmol) of di-n-propyl carbonate were weighed successively under argon into a 300 ml autoclave with stirrer, which was placed into a thermostated heating jacket. After the mixture had been stirred at 150° C. for 12 h, the mixture was cooled to 50° C. rinsed out of the autoclave with 250 ml of toluene and admixed with 50 ml of water. On completion of phase separation, the organic upper phase was washed once with 50 ml of water and concentrated to dryness. A brown, high-viscosity oil was obtained (25.2 g), which, according to NMR spectroscopy, as well as carbonate residues, comprised both the bisurethane and the intermediate monourethanes in a molar ratio of 67:33.

The invention claimed is:

1. A process for preparing urethanes, comprising
reacting, in the presence of a base as a catalyst, an aromatic diamine with an organic dialkyl carbonate to obtain a urethane, wherein
an alkyl radical of the organic dialkyl carbonate comprises 2-18 carbon atoms and at least one heteroatom, and
the base comprises an alkali metal alkoxide, wherein the alkoxide moiety of the alkali metal alkoxide has at least one heteroatom.

2. The process according to claim 1, wherein the at least one heteroatom of the alkyl radical of the organic dialkyl carbonate is selected from the group consisting of a halogen atom, oxygen, and nitrogen.

3. The process according to claim 1, wherein the base is present in a molar ratio of from 0.05 to 0.5 based on the amino groups.

4. The process according to claim 1, wherein the aromatic diamine does not have any heteroatoms in the aromatic ring.

5. The process according to claim 1, wherein the aromatic diamine is selected from the group consisting of a tolylenediamine, a diaminophenylmethane, a polyaminopolyphenylmethane, m-phenylenediamine, and a mixture thereof.

6. The process according to claim 1, wherein the organic dialkyl carbonate is selected from the group consisting of bis-2-methoxyethyl carbonate, bis-2-ethoxyethyl carbonate, bis-2-butoxyethyl carbonate, bis-2-methoxy-1-methylethyl carbonate, bis-2-methoxy-2-methylethyl carbonate, bis-2-trifluoroethyl carbonate and bis-2-N,N'-dimethylaminoethyl carbonate.

7. The process according to claim 1, wherein the dialkyl carbonate is present in a molar ratio of dialkyl carbonate to amino groups of from 1:1 to 10:1.

8. The process according to claim 1, wherein the alkoxide of the alkali metal alkoxide has from 2 to 18 carbon atoms in the alkyl chain.

9. The process according to claim 1, wherein the alkoxide of the alkali metal alkoxide has from 2 to 7 carbon atoms in the alkyl chain.

10. The process according to claim 1, wherein the alkoxide of the alkali metal alkoxide has from 2 to 18 carbon atoms in the alkyl chain and is unbranched, branched, or cyclic.

11. The process according to claim 1, wherein the alkoxide of the alkali metal alkoxide has from 2 to 7 carbon atoms in the alkyl chain and is unbranched, branched, or cyclic.

12. The process according to claim 1, wherein the at least one heteroatom of the alkyl radical of the organic dialkyl carbonate is selected from the group consisting of fluorine, chlorine, oxygen, and nitrogen.

13. The process according to claim 1, wherein the base is present in a molar ratio of from 0.05 to 0.3 based on the amino groups.

14. The process according to claim 1, further comprising
reacting a product obtained from said reacting with water to form a urethane present in an aqueous phase; and
separating the urethane from the aqueous phase.

15. The process according to claim 1, wherein the alkali metal alkoxide comprised in the base is sodium 2-methoxyethoxide.

16. The process according to claim 1, wherein the base further comprises lithium hexamethyldisilazide.

17. The process according to claim 1, wherein the alkali metal alkoxide comprised in the base is sodium 2-methoxyethoxide and the base further comprises lithium hexamethyldisilazide, where the sodium 2-methoxyethoxide and the lithium hexamethyldisilazide are present as a mixture.

18. The process according to claim 1, wherein the dialkyl carbonate is present in a molar ratio of dialkyl carbonate to amino groups of from 1:1 to 3:1.

19. The process according to claim 1, wherein
the aromatic diamine is selected from the group consisting of tolylenediamine, diaminophenylmethane, a polyaminopolyphenylmethane, and m-phenylenediamine; and
the organic dialkyl carbonate is selected from the group consisting of bis-2-methoxyethyl carbonate, bis-2-ethoxyethyl carbonate, bis-2-butoxyethyl carbonate, bis-2-methoxy-1-methylethyl carbonate, bis-2-methoxy-2-methylethyl carbonate, bis-2-trifluoroethyl carbonate and bis-2-N,N'-dimethylaminoethyl carbonate.

20. The process according to claim 1, wherein
the aromatic diamine is selected from the group consisting of tolylenediamine, diaminophenylmethane, a polyaminopolyphenylmethane, and m-phenylenediamine;
the organic dialkyl carbonate is selected from the group consisting of bis-2-methoxyethyl carbonate, bis-2-ethoxyethyl carbonate, bis-2-butoxyethyl carbonate, bis-2-methoxy-1-methylethyl carbonate, bis-2-methoxy-2-methylethyl carbonate, bis-2-trifluoroethyl carbonate and bis-2-N,N'-dimethylaminoethyl carbonate; and
the alkali metal alkoxide comprised in the base is sodium 2-methoxyethoxide.

21. The process according to claim 1, wherein each alkoxide moiety of said organic dialkyl carbonate and each alkoxide moiety of said alkali metal alkoxide comprised in said base is the same.

* * * * *